United States Patent [19]
Towle et al.

[11] Patent Number: 5,573,398
[45] Date of Patent: Nov. 12, 1996

[54] DENTAL HYGIENE DEVICE AND CLEANING SOLUTION

[76] Inventors: Lawrence E. Towle, 14721 Caminito Orense Oeste, San Diego, Calif. 92129; Richard A. Cloonan, 16109 Lofty Trail Dr., San Diego, Calif. 92127

[21] Appl. No.: 259,917

[22] Filed: Jun. 10, 1994

[51] Int. Cl.$^6$ ............................... A61G 17/02; A61H 9/00
[52] U.S. Cl. ............................ 433/80; 601/141; 601/162; 15/24
[58] Field of Search ............................... 433/80, 91, 95, 433/100; 601/160, 162, 163, 165; 15/24, 28, 29, 105, 322

[56] References Cited

U.S. PATENT DOCUMENTS

| | | | |
|---|---|---|---|
| 3,134,127 | 5/1964 | Klein | 15/321 |
| 3,211,149 | 10/1965 | Fono | 128/232 |
| 3,566,869 | 3/1971 | Crowson | 128/66 |
| 3,731,675 | 5/1973 | Kelly | 128/62 |
| 4,181,997 | 1/1980 | O'Rourke | 15/24 |
| 4,264,592 | 4/1981 | Xhajanka | 424/195 |
| 4,340,365 | 7/1982 | Pisanu | 433/80 |
| 4,564,519 | 1/1986 | Pellico et al. | 424/48 |
| 4,672,953 | 1/1987 | DiVito | 128/66 |
| 4,903,688 | 2/1990 | Bibby et al. | 601/162 |
| 4,991,570 | 2/1991 | Bullard | 128/66 |
| 5,137,723 | 8/1992 | Yamamoto et al. | 424/400 |
| 5,145,367 | 9/1992 | Kasten | 433/84 |
| 5,258,173 | 11/1993 | Waterfield | 424/49 |
| 5,275,803 | 1/1994 | Dawson | 424/52 |
| 5,458,563 | 10/1995 | Stewart | 601/162 |
| 5,463,792 | 11/1995 | Hogan et al. | 433/91 X |

*Primary Examiner*—Nicholas D. Lucchesi
*Attorney, Agent, or Firm*—Fitch, Even, Tabin & Flannery

[57] ABSTRACT

A dental hygiene device has a brush assembly and a control unit. The brush assembly has a handle with suction and irrigation conduits passing therethrough. A brush head has two or more parallel rows of bristles. Suction and irrigation ports are positioned between the rows and coupled to the suction and irrigation conduits. Suction and irrigation tubes are coupled to the suction and irrigation conduits. The control unit has an irrigation outlet coupled to the irrigation tube and an irrigation pump, and a supply reservoir coupled to the irrigation pump. The supply reservoir contains a dental hygiene solution that is pumped from the supply reservoir through the irrigation outlet into the irrigation tube. The irrigation tube transmits the solution to the irrigation conduit and then to the irrigation port, where it is expelled. A suction inlet is coupled to the suction tube, and a suction pump is coupled to the suction inlet. A waste reservoir is coupled to the suction pump, which suctions the solution into the suction port to the suction tube, which transmits the solution to the suction inlet. The suction pump draws the solution from the suction inlet and expels the solution into the waste reservoir. The solution is an aqueous solution of sodium fluoride, from 0.5 to 1.0 milligrams per fluid ounce; and ascorbic acid from 350 to 425 times, bioflavinoids from 3 to 4.5 times, calcium ascorbate from 19 to 20 times, magnesium ascorbate from 9 to 10.5 times, and potassium ascorbate from 19 to 20 times the sodium fluoride concentration.

15 Claims, 4 Drawing Sheets

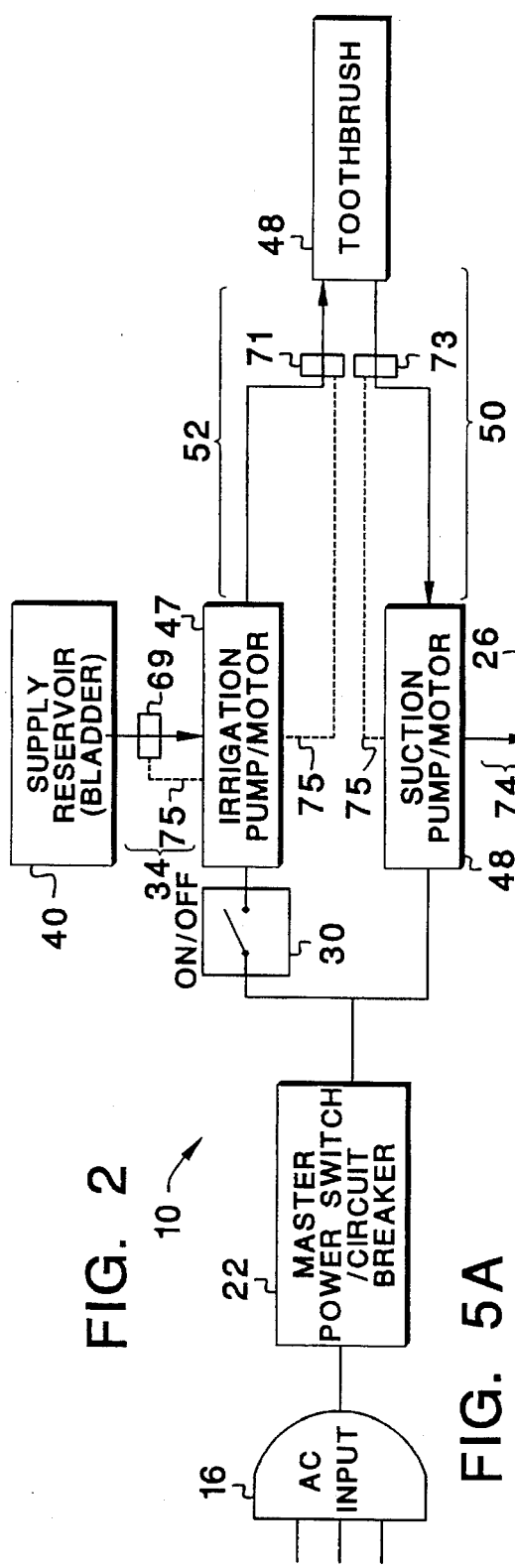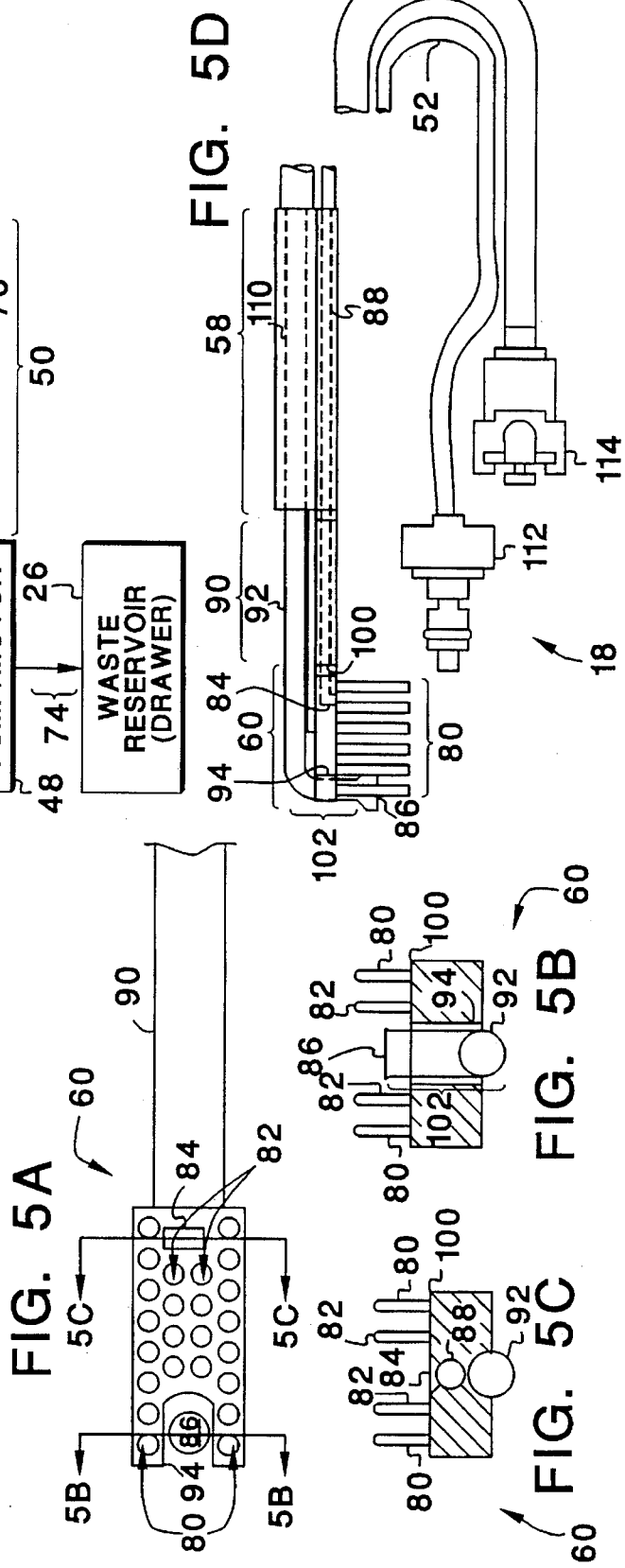

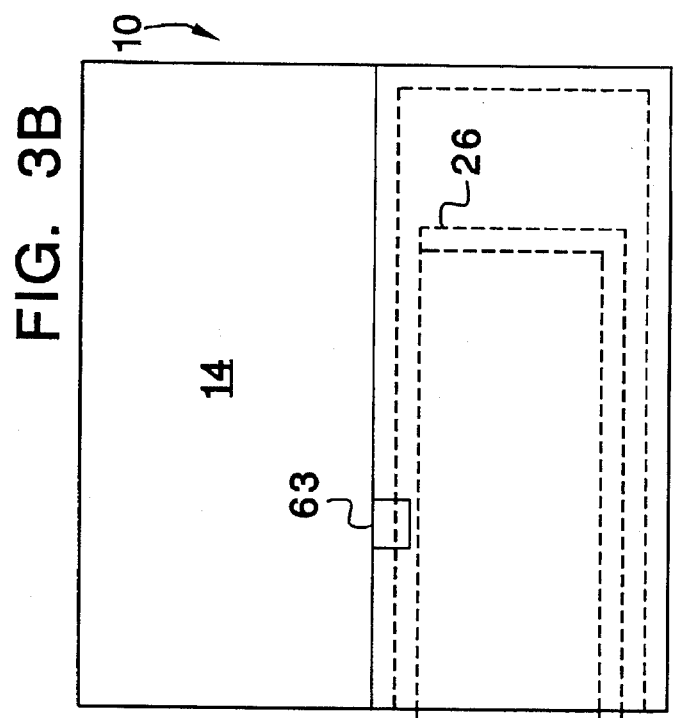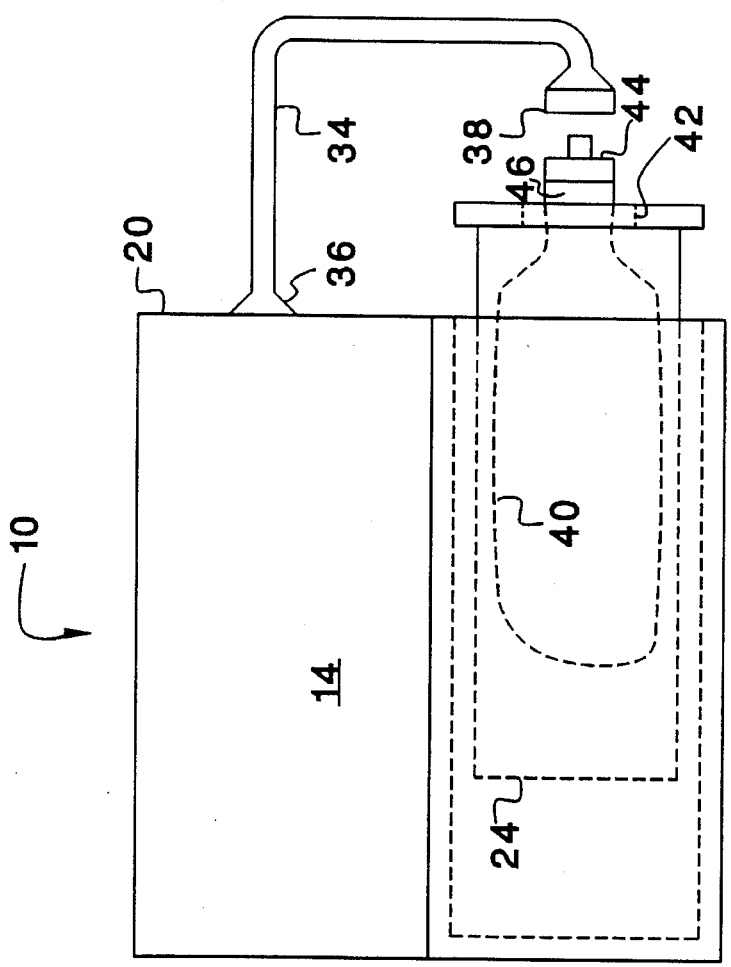

DENTAL HYGIENE DEVICE AND CLEANING SOLUTION

BACKGROUND OF THE INVENTION

The present invention relates to dental hygiene, and more particularly to the cleaning of teeth in humans and other animals. Even more particularly, the present invention relates to a cleaning solution and a device for irrigating human or other animal teeth with fresh cleaning solution and simultaneously suctioning off spent cleaning solution.

The practice of oral hygiene in hospitals, skilled nursing facilities, home health care and the like has always been a rather vague and ill defined procedure. Some people in such institutions are, of course, able to care for themselves by using conventional tooth brushes and commercially available oral hygiene products such as toothpaste, mouth washes, and the like. However, others both in and out of such institutions are largely or totally dependent on others. For example, people suffering from arthritis, stroke victims, and other medically compromised people, may find it difficult to hold and manipulate a tooth brush while other more severely ill people, such as senile or comatose patients, simply cannot maintain their own oral hygiene programs.

Those people who find it difficult to hold and manipulate a conventional tooth brush are very often ineffective when it comes to accomplishing adequate oral hygiene. Similarly, those attempting to help the people who are unable to help themselves, such as the staff personnel of a hospital or nursing home, or the family of such a person, are not trained in the techniques needed for administering proper oral hygiene to others. And, it is very awkward, messy, and otherwise difficult for untrained medical or lay people to help others with the needed oral hygiene. As a result, very often even in medical institutions, the practice of oral hygiene is inadequate and in some cases, non-existent.

Thus, what is needed is a portable device for cleaning human or other animal teeth, that can be easily utilized by untrained medical personnel in a variety of settings, including in health care facilities, rest homes, or residences.

In addition to the needs for a device that can be used for cleaning teeth, there is a need for a dental hygiene material that is suitable for use with such device. Unfortunately, the relatively thick cleaning pastes that are commonly available for dental hygiene are difficult for some people in hospitals, skilled nursing facilities and home health care to apply. Furthermore, such pastes are difficult for such people to expel after having performed oral hygiene. Thus, a dental hygiene material that is in a liquid form that can be easily and automatically irrigated into a person's mouth and simultaneously suctioned away, while still providing for plaque and debris removal, and for breath freshening, would be advantageous.

The present invention advantageously addresses the above and other needs.

SUMMARY OF THE INVENTION

The present invention addresses the needs above as well as other needs by providing a cleaning solution and a portable device for irrigating human or other animal teeth with fresh cleaning solution and simultaneously suctioning off spent cleaning solution.

The invention can be characterized as a portable dental hygiene device including an irrigation/suction brush and a control unit. The irrigation/suction brush includes a handle having a suction conduit passing longitudinally through the handle and an irrigation conduit also passing longitudinally through the handle. A brush head is coupled to a head end of the handle, and has at least two parallel rows of bristles protruding from it. A suction port is interposed between the two parallel rows of bristles at one end of the two parallel row of bristles, and is coupled to the suction conduit at a head end of the suction conduit. An irrigation port is interposed between the two parallel rows of bristles at another end of the two parallel rows of bristles, and is coupled to the irrigation conduit at a head end of the irrigation conduit. A suction tube is coupled to the suction conduit at a handle end of the suction conduit, and an irrigation tube is coupled to the irrigation conduit at a handle end of the irrigation conduit.

The control unit includes an irrigation outlet detachably coupled to the irrigation tube, and an irrigation pump coupled to the irrigation outlet. A supply reservoir is detachably coupled to the irrigation pump. The supply reservoir contains a dental hygiene solution, and the irrigation pump draws the dental hygiene solution from the supply reservoir and pumps the dental hygiene solution through the irrigation outlet into the irrigation tube. The irrigation tube transmits the dental hygiene solution to the irrigation conduit and to the irrigation port, and the dental hygiene solution is expelled through the irrigation port. A suction inlet is detachably coupled to the suction tube, and a suction pump is coupled to the suction inlet. A waste reservoir is coupled to the suction pump, which suctions a portion of the dental hygiene solution into the suction port to the suction tube. The suction tube transmits the suctioned portion to the suction inlet, and the suction pump expels the suctioned portion into the waste reservoir.

The present invention also includes a dental hygiene solution that includes (a) an aqueous solution of sodium fluoride, from 0.5 to 1.0 milligrams per fluid ounce; (b) ascorbic acid from 350 to 425 times the sodium fluoride concentration; (c) bioflavinoids from 3 to 4.5 times the sodium fluoride concentration; (d) calcium ascorbate from 19 to 20 times the sodium fluoride concentration; (e) magnesium ascorbate from 9 to 10.5 times the sodium fluoride concentration; and (f) potassium ascorbate from 19 to 20 times the sodium fluoride concentration.

It is therefore a feature of the invention to provide a portable dental hygiene device for conveniently, easily and safely irrigating and suctioning a dental hygiene solution to and from human or animal teeth.

It is an additional feature of the invention to provide such a dental hygiene device that includes a brush having two or more rows of bristles and that expels dental hygiene solution from an irrigation port from between and at the one end of the two or more rows of bristles.

It is another feature of the invention to provide such a dental hygiene device and brush that suctions the portion of the dental hygiene solution into the suction conduit from between and at the other end of the two rows of bristles.

It is a further feature of the invention to perform such expulsion and such suctioning simultaneously.

It is an added feature of the invention to provide a dental hygiene solution suitable for use in the dental hygiene device.

It is a supplementary feature of the invention to provide a dental hygiene device as described that is portable, and can be easily taken to patients needing dental hygiene, and safely and conveniently operated at the patient site.

BRIEF DESCRIPTION OF THE DRAWINGS

The above and other aspects, features and advantages of the present invention will be more apparent from the following more particular description thereof, presented in conjunction with the following drawings wherein:

FIG. 2 shows a block diagram of the dental hygiene device of FIG. 1;

FIG. 3A shows a side view of the control unit of the dental hygiene device of FIG. 1 and depicts how a supply drawer thereof is slidably opened to allow replacement of a supply bladder;

FIG. 3B shows another side view of the dental hygiene device of FIG. 1, and depicts a waste drawer thereof;

FIG. 5A shows a top view of a brush head of the brush assembly of the dental hygiene device of FIG. 1;

FIG. 5B shows a cross-sectional view of the brush head taken along line 5B—5B of FIG. 5A;

FIG. 5C shows cross-sectional view of the brush head 60 taken along line 5C—5C of FIG. 5A; and FIG. 5D shows a side view of the brush head of the brush assembly;

Corresponding reference characters indicate corresponding components throughout the several views of the drawings.

DETAILED DESCRIPTION OF THE INVENTION

The following description is of the presently contemplated best mode of practicing the invention. This description is not to be taken in a limiting sense, but is made merely for the purpose of describing the general principles of the invention. The scope of the invention should be determined with reference to the claims.

Figure 1:
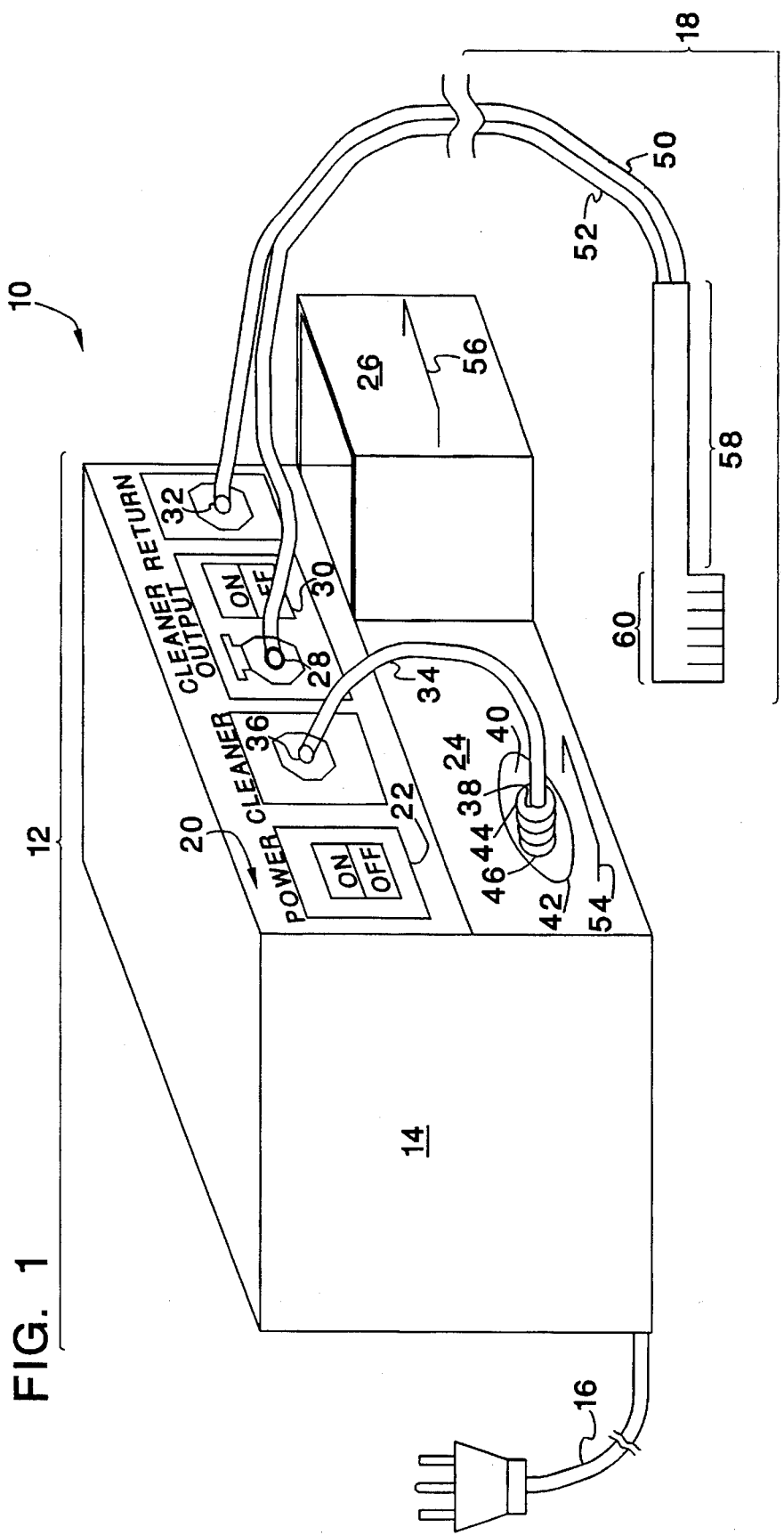
FIG. 1 shows a perspective view of a dental hygiene device made in accordance with the present invention, including a control unit, detachable brush assembly, and power cord.

Referring first to FIG. 1, a perspective view is shown of a dental hygiene device 10 made in accordance with the present invention. The dental hygiene device 10 includes a control unit 12 housed in a housing 14, a power cord 16, and an irrigation/suction brush assembly 18. The control unit 12 has a control panel 20 that includes a main power switch 22, a supply reservoir drawer 24, a waste reservoir drawer 26, an irrigation outlet 28, an irrigation pump switch 30, a suction inlet 32, and a supply tube 34.

The supply tube 34 is coupled at one end 36 to the control panel 20 and at the other end 38 to a collapsible supply bladder 40 that protrudes through an opening 42 in the supply reservoir drawer 24. Preferably, the supply tube 34 is detachably coupled to the supply bladder 40 at a cap 44 of the supply bladder 40, which cap 44 protrudes through the opening 42 in the supply reservoir drawer 24. The cap 44 is a threaded cap that screws onto a cap opening 46 on the supply bladder 40, as is known in the art. The supply bladder 40 is preferably a flexible, disposable, plastic bladder bag. The supply bladder 40 is housed in the supply reservoir drawer 24 with its cap opening 46 protruding through the opening 42 in the supply reservoir drawer 24.

The irrigation/suction brush assembly 18 is detachably coupled to the control panel 20 by a suction tube 50 at the suction inlet 32, and by an irrigation tube 52 at the irrigation outlet 28. The irrigation/suction brush assembly 18 also includes a handle 58 and a brush head 60, as explained more completely below.

The master power switch 22 is used to control whether power received through the power cord 16 is applied to the dental hygiene device 10. The irrigation pump switch 30 is used in combination with the master power switch 22 to control whether such power is also supplied to an irrigation pump (not shown in FIG. 1) within the housing 14, and thereby to control whether a dental hygiene solution is pumped into the irrigation tube 52 through the irrigation/suction brush assembly 18.

The dental hygiene solution is an aqueous solution of sodium fluoride, having from 0.5 to 1.0, e.g., 0.850, milligrams sodium fluoride per fluid ounce of distilled water. The dental hygiene solution also includes ascorbic acid from 350 to 425, e.g., 392.2, times the sodium fluoride concentration; bioflavinoids from 3 to 4.5, e.g., 3.922 times the sodium fluoride concentration; calcium ascorbate from 19 to 20, e.g., 19.61, times the sodium fluoride concentration; magnesium ascorbate from 9 to 10.5, e.g., 9.804, times the sodium fluoride concentration; and potassium ascorbate from 19 to 20, e.g., 19.41 times the sodium fluoride concentration. The dental hygiene solution also preferably includes a flavoring agent such as those flavoring agents commonly used in the art.

An example composition of a dental hygiene solution made in accordance with the present invention, which may be adjusted to the quantity of the fluid being mixed, comprises:

| | |
|---|---|
| distilled water | 6 ounces |
| Vitamin C | 2000 mg |
| Bioflavinoids | 20 mg |
| Calcium Ascorbate | 100 mg |
| Magnesium Ascorbate | 50 mg |
| Potassium Ascorbate | 99 mg |
| Flavoring Agent | 2 drops |
| Sodium Fluoride | 4 drops (each drop contains 1.275 mg of Sodium Fluoride which is equivalent to .125 mg Fluoride ion.) |

The waste reservoir drawer 26 is preferably removable so that it can be easily removed and emptied as needed. The waste reservoir drawer 26 is filled by a suction pump (not shown in FIG. 1) within the housing 14, which suctions the dental hygiene solution from the suction tube 50 and expels it into the waste reservoir drawer 26.

The supply reservoir drawer 24 is also preferably removable so that it can be easily removed when the supply bladder 40 needs to be replaced. A fresh supply bladder can easily be inserted into the supply reservoir drawer 24. Preferably, sealed supply bladders containing the dental hygiene solution as described above may be prepared and sold as a supply component of the device 10. Thus, users of the device 10 need only purchase or otherwise acquire the control unit 12, and then purchase one or more supply bladders, filled with the dental hygiene solution as required. Both the supply reservoir drawer 24 and the waste reservoir drawer 26 have handles 54,56, respectively, to facilitate their opening and closing.

Referring next to FIG. 2, a block diagram is shown of a dental hygiene device 10 made in accordance with the present invention. The power cord 16 is shown coupled to the master power switch 22, which preferably includes a circuit breaker. Also shown are the irrigation pump switch 30, the irrigation pump/motor 47, the supply reservoir 40 (or supply bladder 40), the suction pump/motor 47, the waste reservoir 26 (or waste reservoir drawer 26), the irrigation/suction brush 18, an irrigation valve/irrigation check valve 71, a supply valve/supply check valve 69, and a suction valve/suction check valve 73.

The master power switch 22, through suitable electrical connections, e.g., wires and/or printed circuit boards, provides power from the power cord 16 to the irrigation pump switch 30 and to the suction pump/motor 48. The irrigation pump switch 30 supplies, through suitable electrical connections, power to the irrigation pump/motor 47.

The supply reservoir 40 is coupled to the irrigation pump/motor 47 through the supply tube 34, and supplies the dental hygiene solution to the irrigation pump/motor 47. The irrigation pump/motor 47 is coupled to the irrigation/suction brush assembly 18 via the irrigation tube 52.

The waste reservoir 26 receives spent (waste) dental hygiene solution from the suction pump/motor 48 via a waste tube 74. The suction pump/motor 48 draws the spent dental hygiene solution through the suction tube 50 from the irrigation/suction brush assembly 18.

In operation, when power is supplied to the dental hygiene device 10 through the power cord 16 and master power switch 22, the suction pump/motor 48 draws spent dental hygiene solution through the suction tube 50 from the irrigation/suction brush assembly 18.

Similarly, when the power is applied through the power cord 16 and the master power switch 22, and the irrigation pump switch 30 is placed into an "on" position, the irrigation pump/motor 47 pumps dental hygiene solution from the supply reservoir 40 through the irrigation tube 52 and into the irrigation/suction brush assembly 18. Advantageously, in the event that excessive dental hygiene solution is being supplied to the irrigation/suction brush assembly 18, the irrigation pump switch 30 can be switched into an "off" position thereby terminating the supply of power to the irrigation pump/motor 47 and consequently terminating the pumping of the dental hygiene solution through the irrigation tube 52.

The irrigation/suction brush assembly 18 is detachably connected to the control unit 12 via the check valves 71,73. This detachably advantageously allows several patients, each having his or her own brush assembly 18, to share the same control unit 12.

The supply valve/supply check valve 69 serves two functions. The first function is to close off the supply tube 34 when it is detached from the supply reservoir 40, so that dental hygiene solution in the supply tube 43 does not spill when the supply tube 34 is detached. The second function is to prevent the reverse flow of the dental hygiene solution into the supply reservoir 40 from the supply tube 34, and thereby to prevent contamination of the dental hygiene solution in the supply reservoir 40.

The irrigation valve/irrigation check valve 71 also serves two functions similar to those of the supply valve/supply check valve 69. First, the irrigation valve/irrigation check valve 71 closes off the irrigation tube 52 and the irrigation outlet 28 when the irrigation tube 52 is detached from the irrigation outlet 28, so as to prevent spillage of the dental hygiene solution from the irrigation tube 52 and the irrigation outlet 28. Second, the irrigation valve/irrigation check valve 71 prevents the reverse flow of the dental hygiene solution from the irrigation tube 52 into the irrigation outlet 28, and therefore the contamination of the dental hygiene solution in the irrigation outlet 28, irrigation pump/motor 47, and supply tube 34.

Note that both the supply valve/supply check valve 69, and the irrigation valve/irrigation check valve 71 include at least two integrated valve connectors, one that is coupled to the control panel and another that is coupled to the supply or irrigation tube 34 or 52, respectively. In operation, the two integrated valve connectors are detachably coupled to one another so as to provide for easy detachment of the irrigation/suction brush assembly 18 or supply bladder 40, respectively.

The suction valve/suction check valve 73 also performs two analogous functions. That is, it closes off the suction tube 50 when the suction tube is removed from the suction inlet 32. However, the suction valve/suction check valve 73 will preferably not close off the suction inlet 32 when the suction tube 50 is removed so as to prevent damage to the suction pump/motor 48 in the event the suction pump/motor 48 is operated with the suction tube 50 removed. The suction valve/suction check valve 73 also prevents the reverse flow of the dental hygiene solution from the suction inlet 32 into the suction tube 50, and thereby prevents contamination of the dental hygiene solution in the suction tube 50 with the dental hygiene solution in the suction inlet 32 and suction pump/motor 48.

Note that the suction valve/suction check valve 73 includes an integrated valve connector, and a valve-less connector. The valve-less connector is coupled to the control panel and the integrated valve connector is coupled to the suction tube 50. In operation, the valve-less connector and the integrated valve connector are detachably coupled to one another so as to provide for easy detachment of the irrigation/suction assembly 18.

A suitable irrigation valve/irrigation check valve 71, supply valve/supply check valve 69, and suction valve/suction check valve 73 are available as part no's 69-BUH 22-02, 71-PMCD 16-02 and 73-PMC 42-03 from Colder Products Company of Saint Paul, Minn.

Note that the irrigation valve/irrigation check valve 71, the supply valve/supply check valve 69, and the suction valve/suction check valve 73 are preferably purely mechanical valves, however, they may be automatic solenoid activated valves operated and/or monitored electrically via respective control lines 75.

In this way, dental hygiene solution is simultaneously and automatically supplied to and suctioned from the irrigation/suction brush assembly 18, without the need for the person using the dental hygiene device 10 to manually expel thick dental hygiene paste (e.g., toothpaste).

Referring next to FIG. 3A, a side view is shown of the dental hygiene device 10, and in particular, of the housing 14, the supply reservoir drawer 24, the supply bladder 40, the cap opening 46, the cap 44 and the supply tube 34. As can be seen, the supply tube 34 is attached at one end 36 to the control panel 20 and can be detachably attached to the cap 44 of the supply bladder 40 at the other end 38. The cap 44 and the cap opening 46 of the supply bladder 40 protrude through the opening 42 of the supply drawer 24 to facilitate attachment of the supply tube 34 to the cap 44.

Referring next to FIG. 3B, a side view of the opposite side of the dental hygiene device 10 is shown, and in particular, of the housing 14 and the waste drawer 26 (or the waste reservoir 26). As illustrated, the waste reservoir 26 is slideably removable from the housing 14 so that when the waste drawer 26 becomes full of spent dental hygiene solution, it can be removed from the housing 14 and emptied. Preferably the housing 14 and the waste drawer 26 are made, at least in part, from a transparent material, such as plexiglass, or other clear plastic, so that it can easily be determined through visual inspection whether the waste drawer 26 needs to be emptied.

Also shown in FIG. 3B is a fitting 63 through which the spent dental hygiene solution flows into the waste reservoir. The fitting 63 is described more completely hereinbelow.

Figure 4:
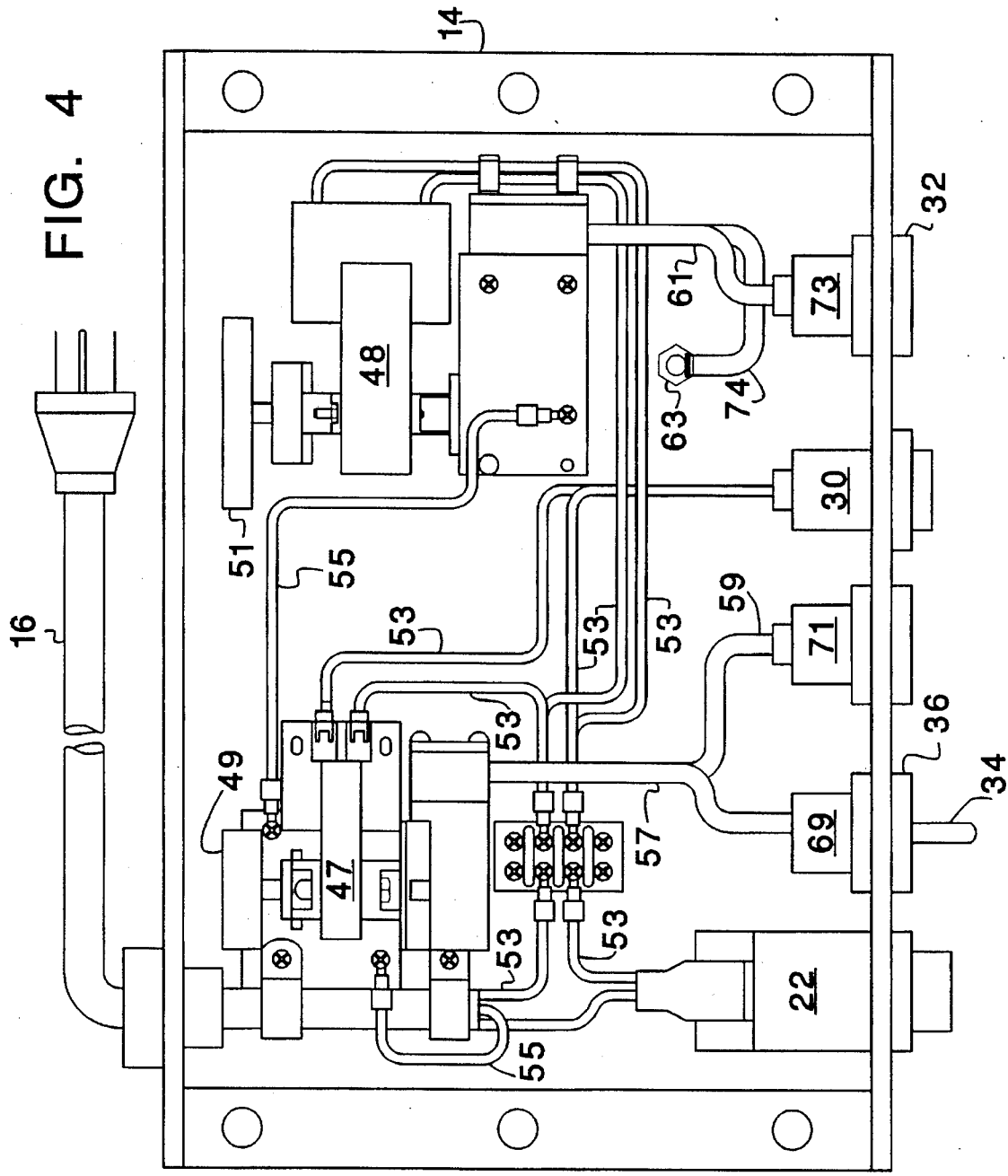
FIG. 4 shows a top view of the dental hygiene device of FIG. 1 with an upper plate removed to expose the components therein.

Referring next to FIG. 4, a top view of the dental hygiene device 10 is shown with an upper panel removed to depict the arrangement of the components used therein. The power cord 16, the housing 14 and the master power switch 22 are shown, along with the irrigation pump/motor 47, the supply tube 34, the irrigation outlet 28, the irrigation pump switch 30, the suction pump/motor 48, the suction inlet 32, and the waste tube 74. Also shown are an irrigation pump/motor cooling fan 49, a suction pump/motor cooling fan 51, power supply wires 53, grounding wires 55, a supply pump tube 57, an irrigation pump tube 59, and a suction pump tube 61. The irrigation valve/irrigation check valve 71, and the suction valve/suction check valve 73 are also shown.

A suitable irrigation pump/motor 47 is available as part no. 5002F-000-FP from ASF Inc. of Norcross, Ga. A suitable suction pump/motor 48 is available as part no. 8010-000-QP from ASF Inc. of Norcross, Ga.

Power is received into the housing 14 via the power cord 16. Power supply wires 53 carry the power to the master power switch 22, the suction pump/motor 48, and the irrigation pump switch 30. The irrigation pump switch 30 carries the power to the irrigation pump/motor 47. When the master power switch 22 is turned on, the suction pump/motor 48 operates, and power is supplied to the irrigation pump switch 30. When both the master power switch 22 and the irrigation pump switch 30 are turned on, the irrigation pump/motor 47 operates. Hence, it is not possible for the irrigation pump/motor 47 to be turned on when the suction pump is turned off.

When operating, the irrigation pump/motor 47 pumps the dental hygiene solution from the supply tube 34 into the supply pump tube 57, through the irrigation pump/motor 47, and out the irrigation pump tube 59 to the irrigation outlet 71. Similarly, when the suction pump/motor 48 operates, the dental hygiene solution is pumped in through the suction inlet 32 into the suction pump tube 61, through the suction pump/motor 48 and out the waste tube. The waste tube 74 is coupled to the fitting 63 that is positioned above the waste reservoir (FIG. 3B). The dental hygiene solution flows from the fitting 63 into the waste reservoir 26 by gravity.

An example of the dental hygiene device has the following dimensions and components:

| | |
|---|---|
| Plastic housing (Control unit) | 6" H, 8 ⅛" W, 6 ¼" D |
| Supply tube (plastic) | .125" ID, .250" OD |
| Irrigation tube (plastic) | .125" ID, .250" OD |
| Suction tube (plastic) | .187" ID, .300" OD |
| Supply reservoir drawer | 2 9/16" H, 5 ½" W, 5 15/16" D |
| Waste reservoir drawer | 2 9/16" H, 2" W, 5 15/16" D |
| Approximate weight (Control unit) | 10 LBS |

Referring next to FIGS. 5A, 5B and 5C, details of the brush head 60 are shown. At least two, and preferably at least four, parallel rows of bristles 80,82 protrude from the bottom of the brush head (normal to the plane of the paper as oriented in FIG. 5A). An irrigation port 84 consists of a slot that is interposed between the outermost two rows of bristles 80 at one end of the rows 80. The slot of the irrigation port 84 is perpendicular to the rows 80. The irrigation port 84 is in fluid communication with an irrigation conduit 88 that is longitudinally within a shaft 90 that is substantially parallel to the rows 80 and attaches the brush head 60 to the handle 58.

A suction port 86, circular in cross section, is interposed between the outermost two rows of bristles 80 at another end of the bristle rows 80. The suction port 86 is coupled to a suction connector 92 that passes outside the shaft 90 and connects to a suction conduit in the handle 58. Unlike the irrigation port 84, which is integral with the brush head 60, the suction port 86 lies in a channel 94 that is formed in the end of the brush head 60 furthest from the shaft 90.

In operation, dental hygiene solution is ejected through the irrigation port 84 under pressure generated by the irrigation pump/motor 47 (FIG. 2). At the same time, spent dental hygiene solution and other debris that are loosened from teeth by the bristles 80,82 and dental hygiene solution are drawn into the suction port 86 by suction that is created by the suction pump/motor 48.

As seen best in FIG. 5B, the bristles 80 protrude from a surface 100 of the brush head 60. The suction nozzle 102 is coupled at one end to the suction port 86 and is coupled at another end to the suction connector 92, as explained more completely below. The suction nozzle 102 protrudes from the surface 100 about half the distance that the outermost two rows of bristles 80 protrude. The bristles 80, 82 protrude out from the surface 100 a distance of about 0.375 in.

As seen best in FIG. 5C, the relative location of the suction connector 92 and the irrigation conduit 88 are shown within the brush head 60. The irrigation port 84 is formed in the brush head 60 by, e.g., machining the brush head 60, which is preferably made from resin or plastic.

Referring next to FIG. 5D, a side view is shown of the irrigation/suction brush 18. The bristles 80 protrude from the surface 100 of the brush head 60, and the suction port 86 and suction nozzle 102 are shown protruding through the channel 94 in the brush head 60. As can be seen, the suction nozzle 102 preferably protrudes about half (50%) as far as the outermost two rows of bristles 80 protrude, although the suction nozzle 102 may protrude one quarter (25%) as far as the outermost two rows of bristles 80 protrude. It is important that an adequate space be provided between a tip of the suction nozzle 102 and the end of the bristles 80 so that the suction nozzle 102 cannot easily be forced against the gums or teeth, and thus blocked from preforming its suction function. At the same time, it is important that the suction nozzle protrude from the surface 100 so that it is positioned close to the gums and teeth so as to facilitate suctioning of the dental hygiene solution and debris. The suction nozzle 102 is integrally coupled to the suction connector 92, which is coupled to the suction conduit 110 that passes longitudinally through the handle 58. The suction conduit 110 is also coupled to the suction tube 50.

Also shown in FIG. 5D is the irrigation port 84 that is coupled to the irrigation conduit 88. The irrigation conduit 88 passes longitudinally through the shaft 90 and the handle 58, and is coupled to the irrigation tube 52. The portion of the irrigation conduit 88 that passes through the shaft 90 and the brush head 60 is also referred to herein as the irrigation duct in order to distinguish it from the irrigation conduit 88, which passes through the handle 58.

In practice, the irrigation tube 52 and suction tube 50 are preferably about six feet long, and are detachably coupled to the irrigation outlet 28 and suction inlet 32, respectively, of the control unit 12. Detachable couplings 112, 114 couple the irrigation tube 52 and the suction tube 50 to the irrigation outlet 28 and suction inlet 32, respectively. The coupling 112 includes one of the integrated valve connectors that are included in the irrigation valve/irrigation check valve 71 and is available as part no. PMCD 16-02 from Colder Products Company of Saint Paul, Minn. The coupling 114 includes the integrated valve connections that is included in the suction valve/suction check valve 73 and is available as part no. PMCD 42-01 from Colder Products Company of Saint Paul, Minn.

The size and weight of the control unit 12 make it possible for the entire device 10 to be readily portable. That is, the device can be easily carried to those in need of dental hygiene, particularly those who may be bed-ridden or are otherwise unable to receive or provide themselves with needed dental hygiene care.

Thus, it is seen that the invention provides an improved dental hygiene device that provides for simultaneous irrigation and suction through an irrigation/suction brush.

It is also seen that the invention provides an improved dental hygiene solution suitable for use with the dental hygiene device described herein.

While the invention herein disclosed has been described by means of specific embodiments and applications thereof, numerous modifications and variations could be made thereto by those skilled in the art without departing from the scope of the invention set forth in the claims.

What is claimed is:

1. A dental hygiene device including:
   an irrigation/suction brush including,
      a handle having a suction conduit passing longitudinally through the handle and an irrigation conduit also passing longitudinally through the handle,
      a brush head coupled to a head end of the handle, the brush head having two parallel rows of bristles protruding from the brush head,
      a suction port that is interposed between the two parallel row of bristles at one end of the two parallel row of bristles, the suction port being coupled to the suction conduit at a head end of the suction conduit,
      an irrigation port that is interposed between the two parallel rows of bristles at another end of the two parallel rows of bristles, the irrigation port being coupled to the irrigation conduit at a head end of the irrigation conduit,
      a suction tube coupled to the suction conduit at a handle end of the suction conduit, and
      an irrigation tube coupled to the irrigation conduit at a handle end of the irrigation conduit; and
   a portable control unit including:
      an irrigation outlet coupled to the irrigation tube,
      an irrigation pump coupled to the irrigation outlet,
      a supply reservoir coupled to the irrigation pump, the supply reservoir containing a dental hygiene solution, the irrigation pump drawing the dental hygiene solution from the supply reservoir and pumping the dental hygiene solution through the irrigation outlet into the irrigation tube, the irrigation tube transmitting the dental hygiene solution to the irrigation conduit and to the irrigation port, the dental hygiene solution being expelled through the irrigation port,
      a suction inlet coupled to the suction tube,
      a suction pump coupled to the suction inlet,
      a waste reservoir coupled to the suction pump, the suction pump suctioning a portion of the dental hygiene solution into the suction port to the suction tube, the suction tube transmitting the portion to the suction inlet, the suction pump drawing the portion from the suction inlet and expelling the portion into the waste reservoir;
   whereby the dental hygiene solution is expelled from the irrigation port from between and at the one end of the two rows of bristles; and
   whereby the portion of the dental hygiene solution is simultaneously suctioned into the suction conduit from between and at the other end of the two rows of bristles.

2. The dental hygiene device of claim 1 wherein said dental hygiene solution includes:
   an aqueous solution of sodium fluoride, from 0.1 to 0.3 milligrams per fluid ounce;
   ascorbic acid from 350 to 425 times the sodium fluoride concentration;
   bioflavinoids from 3 to 4.5 times the sodium fluoride concentration;
   calcium ascorbate from 19 to 20 times the sodium fluoride concentration;
   magnesium ascorbate from 9 to 10.5 times the sodium fluoride concentration; and
   potassium ascorbate from 19 to 20 times the sodium fluoride concentration.

3. The dental hygiene device of claim 1 wherein said irrigation/suction brush includes:
   an irrigation duct passing longitudinally through the brush head, the irrigation duct being coupled at one end to the irrigation port and at another end to the irrigation conduit.

4. The dental hygiene device of claim 3 wherein said irrigation/suction brush further includes:
   a suction connector passing outside the brush head, the suction connector being coupled at one end to the suction port and at another end to the suction conduit.

5. The dental hygiene device of claim 3 wherein said irrigation/suction brush includes:
   a surface from which said two rows of bristles protrude;
   a slot in the surface, the slot comprising the irrigation port and being oriented substantially perpendicular to said two parallel rows of bristles.

6. The dental hygiene device of claim 5 wherein said irrigation/suction brush includes:
   a suction nozzle having one end that protrudes from said surface surface, said suction port being at the one end of the suction nozzle that protrudes.

7. The dental hygiene device of claim 6 wherein said suction nozzle protrudes from said surface at least 25% as far as said two parallel rows of bristles protrude.

8. The dental hygiene device of claim 6 wherein said suction nozzle protrudes from said surface at least 50% as far as said two parallel rows of bristles protrude.

9. The dental hygiene device of claim 5 wherein said irrigation/suction brush includes:
   a channel passing through said brush head, the channel having a longitudinal axis that is substantially normal to said surface, and being positioned opposite said handle, the channel having two open ends;
   a suction nozzle positioned in the channel and having one end that protrudes from one of the two open ends of the channel, the one of the two open ends being at said surface, the suction nozzle thereby protruding from said surface, said suction port being at the one end of the suction nozzle that protrudes from said surface.

10. The dental hygiene device of claim 3 wherein said irrigation/suction brush further includes:

a suction connector passing outside the brush head, the suction connector being coupled at one end to the suction conduit, said suction nozzle protruding from another of the two open ends of the channel and being integrally coupled at another end of the suction nozzle to another end of the suction connector, the suction connector and said suction nozzle having longitudinal axes that are substantially perpendicular to one another.

11. The dental hygiene device of claim 1 wherein said control unit includes:

an irrigation valve that selectively stops said dental hygiene solution from being pumped through said irrigation outlet, said irrigation tube being detachably coupled to the irrigation outlet, the irrigation value stopping said dental hygiene solution from being pumped when said irrigation tube is detached from said irrigation outlet and allowing said dental hygiene solution to be pumped when said irrigation tube is coupled to said irrigation outlet.

12. The dental hygiene device of claim 1 including:

an irrigation check valve that selectively stops said dental hygiene solution from being pumped through said irrigation outlet, the irrigation check valve allowing said dental hygiene solution to flow in a forward direction through said irrigation outlet toward said irrigation port, and stopping said dental hygiene solution from flowing in a reverse direction through said irrigation outlet from said irrigation port.

13. The dental hygiene device of claim 12 including:

a suction check valve that selectively stops said portion of said dental hygiene solution from being pumped through said suction inlet, the suction check valve allowing said portion of said dental hygiene solution to flow in a forward direction through said suction inlet from said suction port, and stopping said portion of said dental hygiene solution from flowing in a reverse direction through said suction inlet toward said suction port.

14. The dental hygiene device of claim 1 wherein said supply reservoir includes:

a collapsible bladder that is coupled to the irrigation pump, the collapsible bladder contains the dental hygiene solution, said irrigation pump drawing the dental hygiene solution from the collapsible bladder, the collapsible bladder collapsing as the dental hygiene solution is drawn from the collapsible bladder.

15. The dental hygiene device of claim 14 including:

a supply check valve that selectively stops said dental hygiene solution from being drawn from said collapsible bladder, the supply check valve allowing said dental hygiene solution to flow in a forward direction from said collapsible bladder toward said irrigation pump, and stopping said dental hygiene solution from flowing in a reverse direction from said irrigation pump to said collapsible bladder.

* * * * *